(12) United States Patent
Weisbart et al.

(10) Patent No.: US 8,160,898 B2
(45) Date of Patent: *Apr. 17, 2012

(54) IDENTIFICATION OF SPECIALTY DRUGS

(75) Inventors: Edmond Weisbart, Olivette, MO (US); Andrew Behm, Minneapolis, MN (US); Aimee Tharaldson, Woodbury, MN (US); Steven Miller, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/217,471

(22) Filed: Aug. 25, 2011

(65) Prior Publication Data

US 2011/0307271 A1   Dec. 15, 2011

Related U.S. Application Data

(63) Continuation of application No. 12/011,621, filed on Jan. 28, 2008, now Pat. No. 8,050,940.

(51) Int. Cl.
*G06Q 10/00* (2012.01)

(52) U.S. Cl. .............................. 705/2; 705/3

(58) Field of Classification Search .................... 705/2, 3
See application file for complete search history.

(56) References Cited

U.S. PATENT DOCUMENTS

| | | | |
|---|---|---|---|
| 6,826,536 B1 * | 11/2004 | Forman | 705/4 |
| 7,765,108 B2 * | 7/2010 | Goodall et al. | 705/2 |
| 2006/0247968 A1 * | 11/2006 | Kadry | 705/14 |
| 2007/0088569 A1 * | 4/2007 | Berkelhamer et al. | 705/2 |
| 2007/0214014 A1 * | 9/2007 | Suwalski et al. | 705/3 |

* cited by examiner

*Primary Examiner* — Vivek Koppikar
*Assistant Examiner* — Edward Winston, III
(74) *Attorney, Agent, or Firm* — Bryan Cave, LLP

(57) ABSTRACT

Methods for determining whether a drug is a specialty drug, methods for creating tools to be used in making the determination, and the tools themselves are disclosed. The overall value of a drug depends on the drug's attribute values with respect to each of a set of drug attributes (concerning, e.g., the drug's route of administration, targeted disease, possible adverse reactions, risk of toxicity, cost, need for patient compliance with the treatment regime, and handling, preparation, and/or storage requirements. If the overall value or its partial overall values meet certain criteria, the drug is deemed to be a specialty drug.

17 Claims, 2 Drawing Sheets

| Attributes of Specialty Drugs | Characteristics | Points | Examples |
|---|---|---|---|
| Care | | | |
| A Specialized requirements for clinical services (expertise, resources or technology) to support patient understanding and/or self-management of their condition. | Highly specialized clinical expertise required to support patient understanding and/or self-management of their complex and rare condition | 2 | Rare conditions/few experts: Hemophilia, Enzyme deficiencies (Fabry's, Pompe, Hunter syndrome), Pulmonary arterial hypertention (PAH) |
| | Specialized clinical expertise required to support patient understanding and/or self-management of their complex or rare condition | 1 | Hepatitis C, MS, RA, RSV, HIV, Cancer, Growth deficiency |
| | General clinical expertise required to support patient understanding and/or self-management of their condition | 0 | Hepatitis B immune globulin |
| B Specialized requirements for intensive patient training specific to medication administration or specialized requirements for product administration | Very intensive patient training required specific to medication administration (i.e. self-administered SQ injection / infusion, self-administered IM injection) or highly specialized requirements for product administration by a healthcare professional (IV infusion) | 2 | Vivaglobin (SQ infusion), Flolan (IV infusion pump), Advate (IV infusion), Amevive (IM injection), Avastin (IV infusion) |
| | Moderately intensive patient training required specific to medication administration or moderately specialized requirements for product administration by patients (i.e. specialized nebulization, specialized oral administration) | 1 | Ventavis (Nebulization) |
| | Average level of patient training required specific to medication administration or no specialized requirements for product administration (i.e. most oral administration, topical administration) | 0 | Gleevec (Oral), Nexavar (Oral) |
| C Specialized requirements for intensive clinical monitoring to decrease the potential for drug toxicity and to monitor for therapeutic effect. | Very intensive clinical monitoring (e.g., frequent blood tests, short duration of time until follow-up) required, including during drug administration, due to highly toxic and/or commonly occuring adverse drug reactions. | 2 | Flolan, Lovenox, Advate, Procrit, Pegylated Interferon, Ribavirin |
| | Moderately intensive clinical monitoring required, including during drug administration, due to moderately toxic and/or less commonly occuring adverse drug reactions. | 1 | Dacogen, Revlimid, Sprycel, Enbrel |
| | Average level of clinical monitoring (e.g., annual follow up and call in if any side effects) required to decrease the potential for drug toxicity | 0 | Gleevec |

FIG. 1a

| Attributes of Specialty Drugs | Characteristics | Points | Examples |
|---|---|---|---|
| Service | | | |
| D Specialized requirements for compliance assistance to facilitate therapeutic goals. | Compliance assistance necessary in order to facilitate therapeutic goals (i.e., life-saving, immediate impact) | 2 | Flolan, Advate |
| | Compliance assistance recommended in order to facilitate therapeutic goals (i.e., life-saving, long-term impact) | 1 | Pegylated Interferon, Humira, Rebif, Fuzeon, Gleevec, Orthoclone OKT-3 |
| | Compliance assistance optional in order to facilitate therapeutic goals (i.e., life enhancing) | 0 | Botox Cosmetic |
| E Specialized requirements for product handling, preparation and storage. | Highly specialized requirements (e.g., temperature, storage) for product handling | 2 | Doxil (IV), Ellence (IV), Advate |
| | Moderately specialized requirements (i.e. refrigeration) for product handling | 1 | Avonex, Neupogen |
| | No specialized requirements for product handling | 0 | Revatio, Ribavirin |
| Access | | | |
| F Supplied through a limited distribution channel | Medication only available through limited distribution channel | 0 to 10 (to total 10) | Iressa, Elaprase, Increlex, Vivaglobin |
| | Medication available through open distribution channel | 0 | Enbrel, Rebif, Revatio |

FIG. 1b

IDENTIFICATION OF SPECIALTY DRUGS

BACKGROUND OF THE INVENTION

This invention relates to methods of identifying specialty drugs, to methods of creating tools to be used in identifying specialty drugs, and to tools used in the identification of specialty drugs.

Pharmacy benefit managers ("PBMs") administer drug benefit programs for employers, managed care organizations, third-party health plan administrators, purchasing coalitions, and other groups who provide and/or offer health care benefits to a group of individuals. Historically, PBMs were involved primarily in processing or adjudicating claims for reimbursement for purchases of pharmaceuticals. More recently, PBMs have become involved in broader aspects of patient care.

To that end, many PBMs have developed and/or acquired "specialty pharmacies." A specialty pharmacy has been variously described as: a pharmacy, the services of which are used by patients with acute or chronic conditions that can be treated at home, in a physician's office, or at specialized infusion sites (e.g., Walgreen's); a company that works with customers to manage use of high-cost drugs used to treat chronic diseases (e.g., Magellan Health Services); a pharmacy that provides "full-service care to patients requiring special prescription needs for challenging and long-term health conditions" (e.g., CVS, describing Stadtlander in its acquisition of that company); and a provider of pharmacy services for people with complex chronic health conditions (e.g., BioScrip, describing Chronimed Inc.). A principal theme in these descriptions is that there is something special in the level of care provided and/or the type of pharmaceutical involved in the care.

Drugs provided by a specialty pharmacy or otherwise designated as "specialty pharmaceuticals" or "specialty drugs" may be subject to pricing guidelines that are different than for other drugs covered under a health plan. For example, a non-specialty drug might be priced by a PBM to its client at a benchmark price less a percentage A, whereas a specialty drug might be priced at a benchmark price less a percentage B. Furthermore, specialty drugs (which, in some cases are administered by a physician at his or her office) may be provided as part of a patient's medical benefit, as opposed to the patient's pharmaceutical benefit. In addition, a drug dispensed as a specialty drug may be provided with a higher level of care and/or patients who receive specialty drugs may be afforded access to resources not available for patients who receive non-specialty drugs. Because of these distinctions, whether a drug is a specialty drug is often important to PBMs, customers of PBMs, and/or to the patients covered by drug benefit programs managed by PBMs. As indicated below, the significance of whether a drug is a specialty drug is far-reaching.

Historically, classification of a drug as a "specialty drug" has been quite subjective. One definition of "specialty drug" encompassing various criteria that have been used for classification of a drug as a specialty drug might be "an injectable, infused, oral, or inhaled drug having one or more of the following characteristics: (1) a requirement for frequent dosing adjustments and intensive clinical monitoring to decrease the potential for drug toxicity and increase the probability for beneficial treatment outcomes; (2) a need for intensive patient training and compliance assistance to facilitate therapeutic goals; (3) limited or exclusive availability and distribution; (4) specialized handling and/or administration requirements; and (5) cost in excess of $500 for a 30-day supply." CuraScript, Inc., 2004 *Specialty Pharmacy Management Guide & Trend Report* (June, 2005). Such a definition may make it difficult to explain to a customer or plan participant why one particular drug is classified as a specialty drug but another is not. That in turn makes medical care cost decisions less transparent and comprehensible and tends to harm a PBM's relationship with its customers and the plan participants.

Because classification of a drug as a "specialty drug" may affect, among other things, (1) pricing of the drug, (2) determination of whether the drug is provided as part of a prescription benefit or medical benefit, and/or (3) the level of care and/or services provided in connection with sale, dispensing, administration, distribution, and/or monitoring of the drug and/or its apparent effectiveness, whether or not a drug is classified as a "specialty drug" may be quite important.

Thus, there is a need for a method of identifying specialty drugs that ideally: (1) is more objective than current methods, (2) is more transparent than current methods and/or is capable of being understood more readily than current methods, e.g., by a customer of a PBM and/or a participant in a pharmacy benefit plan administered by a PBM, (3) produces relatively consistent determinations of whether or not a drug is a specialty drug when the method is employed by different users, and (4) is easily implemented to (a) identify a set of specialty drugs, (b) evaluate newly-approved drugs for their specialty drug status, and (c) re-evaluate drugs for their specialty drug status with changing circumstances.

BRIEF SUMMARY OF THE INVENTION

An invention having various embodiments that meet one or more of those needs has now been developed. Embodiments of the present invention include methods for determining whether a drug is a specialty drug, methods for creating tools to be used in determining whether a drug is a specialty drug, and the tools themselves.

Embodiments of the invention permit identification of specialty drugs in ways that are significantly less subjective (i.e., are more objective) than those of previous methods and/or provide much greater levels of transparency to purchasers of specialty drugs and those otherwise interested in the sale, dispensing, administration, and/or distribution of specialty drugs. Thus, customers of a PBM or participants in a pharmacy benefit program managed by a PBM can better understand why a particular drug is or is not classified as a specialty drug and, therefore, understand differences in, for example, the level of service provided in connection with the drug. Embodiments of the invention can provide more consistent determinations of whether or not drugs are specialty drugs when used by a variety of users than previous methods and/or can be more easily implemented to identify drugs that are specialty drugs than previous methods.

In one aspect, the invention concerns a method for determining whether a drug is a specialty drug, drugs having drug attributes and characteristics within each attribute, the method comprising the steps:

(a) obtaining a tool for use in identifying specialty drugs, the tool comprising the following items: (i) a set of drug attributes that are relatively more important for determining whether a drug is a specialty drug; (ii) one or more criteria for determining the attribute value of a drug for each of the relatively more important drug attributes; (iii) one or more criteria for determining the overall value of a drug based on the attribute values; and (iv) one or more criteria for determining whether a drug is a specialty drug based on the overall value;

(b) determining for the drug an attribute value for each of the relatively more important drug attributes by applying the criteria of item (ii) of the tool to the characteristics of the drug;

(c) determining for the drug an overall value by applying the criteria of item (iii) of the tool to the attribute values of the drug; and (d) determining whether the drug is a specialty drug by applying the criteria of item (iv) of the tool to the overall value of the drug.

In another aspect, the invention concerns a method for determining whether the drugs in a therapy class of drugs are specialty drugs, drugs having drug attributes and characteristics within each attribute, the method comprising the steps:

(a) obtaining a tool for use in identifying specialty drugs, the tool comprising the following items: (i) a set of drug attributes that are relatively more important for determining whether a drug is a specialty drug; (ii) one or more criteria for determining the attribute value of a drug for each of the relatively more important drug attributes; (iii) one or more criteria for determining the overall value of a drug based on the attribute values; and (iv) one or more criteria for determining whether the drugs in a therapy class comprising two or more drugs are specialty drugs based on the overall values of two or more drugs;

(b) identifying two or more drugs within that therapy class;

(c) determining for each of the drugs identified in step (b) an attribute value for each of the relatively more important drug attributes by applying the criteria of item (ii) of the tool to the characteristics of the drug;

(d) determining for each of the drugs identified in step (b) an overall value by applying the criteria of item (iii) of the tool to the attribute values of the drug; and (e) determining whether the drugs in the therapy class are specialty drugs by applying the criteria of item (iv) of the tool to the overall values of the drugs identified in step (b).

In yet another aspect, the invention concerns a method for creating a tool for use in identifying which drugs are specialty drugs, drugs having drug attributes, the method comprising the steps:

(a) establishing which of the drug attributes are relatively more important for determining whether a drug is a specialty drug, thereby producing a set of relatively more important drug attributes;

(b) establishing one or more criteria for determining the attribute value of a drug for each of the relatively more important drug attributes;

(c) establishing one or more criteria for determining the overall value of a drug based on the attribute values for that drug; and (d) establishing one or more criteria for determining whether a drug is a specialty drug based on the overall value of the drug.

In a further aspect, the invention concerns a tool for use in identifying specialty drugs, drugs having drug attributes, the tool comprising:

(a) a set of drug attributes relatively more important for determining whether a drug is a specialty drug; and (b) one or more criteria for determining the attribute value of a drug for each of the relatively more important drug attributes.

The tool desirably further comprises one or more criteria for determining the overall value for a drug based on the attribute values and preferably still further comprises one or more criteria for determining whether a drug is a specialty drug based on the overall value.

Other preferred embodiments include embodiments in which: the overall value comprises the result of adding together one or more of the attribute values of the drug; one or more threshold values are established, against which the overall value may be compared in making the determination of whether a drug is a specialty drug; deciding which threshold value to use from a set of two or more threshold values may be based on, e.g., the cost of the drug; the tool may be pre-existing; the tool may be obtained from a third party; one or more scales (e.g., numerical scales) may be established for one or more of the drug attributes so that one or more values (e.g., numerical values) can be determined for one or more of the attributes (depending on the drug's characteristics), thereby determining (e.g., numerically determining) one or more of the attribute values for the drug; the overall value of a drug comprises two or more parts, one part being, e.g., a number determined by, e.g., numerically combining (or otherwise mathematically combining) some of the drug's attribute values, and another part being, e.g., a cost or cost range for the drug; and/or the relatively more important drug attributes include one or more of the following: (i) physical attributes, (ii) route of administration, (iii) level of patient training required to understand and/or implement the route of administration, (iv) uniqueness of the route of administration, (v) means of preparation of a drug for delivery to the patient, (vi) means of preparing a drug for administration to the patient, (vii) cost, (viii) storage requirements, (ix) handling requirements, (x) delivery requirements, (xi) manufacturer, (xii) availability, (xiii) distribution channels, (xiv) potential toxicity, (xv) level of incidence and/or severity of adverse reactions, (xvi) extent to which compliance with a treatment regime regarding administration will affect treatment outcomes, (xvii) extent to which patient support is necessary to insure compliance with a treatment regime, (xviii) conditions a drug may be used to treat, (xix) level of clinical expertise required to understand conditions a drug may be used to treat, (xx) pervasiveness of conditions a drug may be used to treat, and (xxi) therapy class of conditions the drug may be used to treat.

Embodiments of the present invention can provide one or more of the above-described features and one or more of the above-described benefits to PBMs and their customers and plan participants. Still other features and benefits will be apparent to those skilled in the art.

BRIEF DESCRIPTION OF THE DRAWINGS

To facilitate further description of the invention, the following drawing is provided in which:

FIG. 1 (FIGS. 1a and 1b together) illustrates a tool according to an embodiment of the invention.

This drawing is provided for illustrative purposes and should not be used to unduly limit the scope of the claims.

DETAILED DESCRIPTION OF THE INVENTION

A drug might be defined as a "specialty drug" if it is dispensed through a specialty pharmacy. As indicated above, however, definitions of "specialty pharmacy" are often vague and inconsistent. Furthermore, a definition of "specialty pharmacy" provides only a generalized understanding of what sort of drugs might be dispensed by a specialty pharmacy.

The present invention does not rely on any definition of "specialty pharmacy" to determine whether a drug is a "specialty drug." Instead, the present invention puts the focus on the characteristics of a particular drug and its uses. A drug classified as a specialty drug using an embodiment of this invention can then be dispensed with special consideration for its method of distribution and/or delivery and/or with special consideration for the patient care associated with the drug.

Thus, a specialty pharmacy may be a pharmaceutical distribution center that is considered to be a specialty pharmacy by those skilled in the art or any pharmacy or other pharmaceutical distribution, administration, support center, or other entity that accommodates special considerations for the methods of distribution and/or delivery of a drug and/or special considerations for patient care associated with such drug and/or the conditions treated by such drug and/or otherwise participates in the distribution and/or administration of the drug. Furthermore, it will be understood by those skilled in the art that a specialty pharmacy need not occupy a distinct physical space.

"Special" indicates a service or characteristic that would be understood by one skilled in the art to be a service or characteristic not typically provided in connection with or associated with dispensing and/or administering a drug and/or in connection with or associated with providing support to a patient to whom the drug is administered and/or to that patient's caregiver(s). For example, a typical delivery mechanism might be mailing using United States Postal Service standard first-class service whereas a "special" delivery mechanism might involve use of a more expedited delivery service and/or making arrangements prior to delivery with the patient, the patient's caregiver, or other appropriate party for a specific time and place to receive the delivery. By way of further example, typically, when a pharmaceutical is dispensed, the patient will have access to a pharmacist to address his or her questions regarding the dispensed drug. "Special" access might include access to a pharmacist and/or other health care specialist with particular expertise in the dispensed drug and/or the condition treated by the drug.

One skilled in the art will immediately recognize the benefit of using specialized distribution, administration, support, etc. for and in connection with certain drugs as compared to the distribution, administration, support, etc. typically provided for most drugs. Thus, embodiments of the present invention allow one skilled in the art to determine which drugs may benefit from more specialized distribution, administration, support, etc. (namely, specialty drugs).

Drug Attributes and Characteristics of Individual Drugs

Drugs have drug attributes. An individual drug will have characteristics that define the drug in the context of each drug attribute. For example, one attribute is color and red is a possible characteristic for the attribute "color."

The term "drug attribute" generally refers to any aspect by which a drug can be defined and/or described, i.e., a category comprising or defined by a set of characteristics (e.g., the drug's dosage form is red, blue, green, orange, or white in color). Thus, drug attributes include any aspects of or relating to drugs and/or their use and/or the conditions treated by them and/or their storage and/or their distribution and/or their preparation, including but not limited to: (i) physical attributes, (ii) route of administration, (iii) level of patient training required to understand and/or implement the route of administration, (iv) uniqueness of the route of administration, (v) means of preparing a drug for delivery to the patient, (vi) means of preparing a drug for administration to the patient, (vii) cost, (viii) storage requirements (e.g., to maintain efficacy), (ix) handling requirements, (x) delivery requirements, (xi) manufacturer, (xii) availability, (xiii) distribution channels, (xiv) potential toxicity, (xv) level of incidence and/or severity of adverse reactions, (xvi) extent to which compliance with a treatment regime regarding administration will affect treatment outcomes, (xvii) extent to which patient support is necessary to insure compliance with a treatment regime, (xviii) conditions a drug may be used to treat, (xix) level of clinical expertise required to understand conditions a drug may be used to treat, (xx) pervasiveness (frequency or incidence) of conditions a drug may be used to treat, and (xxi) therapy class, e.g., of conditions the drug may be used to treat.

(i) "Physical attributes" include color, odor, dosage form (e.g., tablet, capsule, liquid), size, shape, molecular weight, and/or specific gravity. A drug may thus be characterized by its specific physical attributes, e.g., as a white, circular pill with a diameter of approximately 5 millimeters.

(ii) "Route of administering" (or "route of administration of") a drug refers to the manner in which a drug is provided to the patient. For example, a characteristic of a drug may be that it is administered by ingestion, by injection, by infusion, by inhalation, topically, or that it is administered by another appropriate means. If a more specific set of characteristics is appropriate for use in an embodiment of a method of the present invention in the context of this drug attribute, more specific terms for the various manners in which a drug may be provided to a patient may be used, e.g., "subcutaneous injection" and "intravenous injection" instead of "injection."

(iii) "Level of patient training required to understand and/or implement the route of administration" of a drug is typically related to the route of administering a drug. For example, a drug that is characterized by an ingestion route of administration (e.g., swallowing) may be further characterized as requiring a low level of patient training for understanding and/or implementing administration of the drug. In contrast, a drug that is injected intravenously may have the characteristic of requiring a significant level of patient training for administration. A drug such as Ventavis®, which is administered via specialized nebulization, may have a characteristic of requiring moderate patient training. As a further example, a drug (regardless of the route of administration) may have a characteristic of requiring a higher level of patient training for administration if the timing of administration of the drug is especially critical and/or if tests need to be conducted prior to administration. Furthermore, characteristics of drugs within this attribute may be based upon the level of required patient training that is not otherwise generally provided to patients, e.g., via other traditional health care providers. For example, while administration of certain drugs for patients with diabetes, e.g., insulin, may require a significant level of patient training, that training is widely available in many communities. Thus, this drug attribute could be described as the level of patient training that is not otherwise readily available within the community that is required to understand and/or implement administration of a drug.

(iv) "Uniqueness of the route of administration" of a drug refers to how common the route of administering a particular drug is compared to the routes of administering drugs in general. A particular drug may be characterized, for example, as having a common route of administration (e.g., oral), a somewhat uncommon route of administration (e.g., subcutaneous injection), or an uncommon route of administration (e.g., administration directly into a specific body cavity, tissue, or organ). Referring to the attribute discussed immediately above, the level of patient training required for understanding and/or implementing administration of a drug may be related to the uniqueness of route of administering a drug. If a route of administration is uncommon (regardless of whether it might be characterized as difficult), a patient may require some level of additional training to explain the unfamiliar route of administration of that drug.

(v) "Means of preparing a drug for delivery to the patient" refers to the steps to be taken, typically at a pharmacy, prior to dispensing the drug for delivery to a patient. A drug that is delivered to a patient in the same form that it is received from the manufacturer and with fairly simple dosage guidelines would typically have the characteristic of requiring no additional preparation or specialized care prior to dispensing. Another drug may have the characteristic of requiring mixing, dilution, or other manipulation of and/or modification from the form in which it is received from the manufacturer prior to dispensing. By way of further example, some drugs have the characteristic of requiring detailed weight-based dosing as part of preparing a drug for delivery to a patient.

(vi) "Means of preparing a drug for administration to a patient" refers to steps taken prior to administration of a drug to and/or by a patient. A characteristic of some drugs is that they are administered to and/or by a patient in the form received from the pharmacy (or other provider of the drug). Others prior to administration require manipulation and/or modification of the drug from the form in which it is received from the pharmacy. Drugs that require such modification and/or manipulation may have the characteristic of a higher level of patient training required for understanding and/or implementing administration of the drug.

(vii) "Cost" of a drug may refer to cost to the patient, cost to the PBM, cost to the patient's health care provider, cost to the patient's health care plan, and/or cost to any other payor for the drug. "Cost" may refer to the actual amount paid by the patient, the PBM, the health care provider, the patient's health care plan, the pharmacy, and/or any other payor for the drug, or it may refer to a benchmark used by some or all in the pharmaceutical industry in calculating the actual cost of a pharmaceutical to one or more parties. For example, the "cost" of a drug may refer to its AWP (average wholesale price), its WAC (wholesale acquisition cost), its AMP (average manufacturer's price), its direct cost (applicable for generic drugs), as such terms are known to those in the industry, some percentage or fraction of any of the foregoing, or to some other benchmark (or percentage or fraction thereof) that may be used for pricing now or in the future. "Cost" could refer to a per-unit cost. Preferably, "cost" refers to the cost per a designated period, such as the cost for a 30-day supply. The amount needed for a 30-day supply (or another designated period) could be the amount needed by a particular patient during a 30-day period based on the patient's specific dosage requirements. Alternatively, such amount could be based on an average or otherwise standardized determination of the amount needed for a typical 30-day period. The "cost" of a drug may be characterized as the specific dollar amount of, for example, a 30-day supply of the drug. Alternatively, the "cost" of a drug may be characterized by the cost range within which the drug falls, again, on a per-unit basis or for a designated period of time. For example, one drug may have a characteristic cost of less than $500 for a 30-day supply, another of from $500 to $1000 for a 30-day supply, and a third of more than $1000 for a 30-day supply.

(viii) Drugs have "storage requirements." The particular storage requirement characteristics of a drug usually concern the temperature, humidity, light type (e.g., visible, infra-red) and intensity, and other conditions (e.g., concerning vibration) under which the drug can be stored without appreciably compromising its efficacy (e.g., the drug must be stored within the temperature range of 50 to 70 degrees Fahrenheit). Another storage requirement characteristic of certain drugs may be a limited shelf life relative to other drugs, i.e., an efficacy that diminishes relatively rapidly over time even when the drug is stored under otherwise suitable storage conditions.

(ix) "Handling requirements" of a drug may be related to its storage requirements. For example, if a drug has the characteristic of requiring storage within certain ranges of temperature, humidity, and/or light type and intensity to maintain efficacy, those storage requirements may dictate the handling requirement characteristics of the drug. A drug may also have handling requirement characteristics unrelated to temperature, humidity, and/or light type and intensity, e.g., it may be desirable to avoid excess shaking of the drug.

(x) "Delivery requirements" of a drug constitute an attribute often relevant when the drug will be dispensed to a patient via mail or other delivery service (as opposed to its being picked up at a pharmacy by or on behalf of the patient) and refers to the manner in which the drug should be delivered to reduce the risk of decreasing its efficacy and increase the likelihood of its successful administration. The characteristic delivery requirements of a drug are usually related principally to its storage and handling requirement characteristics. For example, if the efficacy of a drug diminishes rapidly with time, the drug may have the characteristic of requiring delivery in a manner more likely to result in its prompt delivery to a patient and at a time and place when and where it can be promptly and properly administered to the patient. Some drugs may be administered to a patient in a more traditional way, e.g., at a physician's office and/or a specialty administration center, such as an infusion center. In such cases, a delivery requirement characteristic may be a preference for delivery of the drug directly to the site at which it will be administered.

(xi) "Manufacturer" of a drug may refer to the entity at whose facility the drug is produced and/or to the entity that has subcontracted (or otherwise arranged for) production of the drug. Identifying the manufacturer of a drug may be relevant for a variety of reasons, including considering requirements and/or guidelines set by the manufacturer regarding various other drug attributes, such as storage, handling, and/or delivery, monitoring quality control, and/or identifying limited sources for distribution of the drug designated by the manufacturer.

(xii) "Availability" of a drug refers to how readily available the drug is in the marketplace. For example, one drug may have the characteristic of being widely available to patients for whom the drug is prescribed while other drugs may be characterized as prone to shortages.

(xiii) Some drugs are available through a variety of "distribution channels." Others, often as a result of a manufacturer's requirements, are available only through certain distribution channels. Specifically, a manufacturer (or other entity that controls distribution and/or availability of a drug) may limit the distribution of a drug only to those pharmacies that will offer special services in connection with dispensing and/or administering the drug and/or in connection with providing support to a patient to whom the drug is administered and/or to the caregivers of that patient.

(xiv) "Potential toxicity" refers to the likelihood of a drug to cause damage to or illness and/or death of the patient. Characteristics of individual drugs include the drug's being highly toxic, moderately toxic, or mildly toxic.

(xv) "Level of incidence and/or severity of adverse reactions" is another drug attribute. As will be understood by those skilled in the art, adverse effects (generally, harmful and/or undesired effects caused by a drug) have a variety of causes and degrees of severity. Characteristics of individual drugs vary widely. For example, one drug may cause a fairly high incidence of typically mild adverse effects while another may have a low incidence of severe adverse effects. The likely causes of adverse effects can further characterize a particular drug. For example, one drug may be characterized by a high likelihood of severe adverse effects if it is administered within a few hours of administering another drug but a low likelihood of severe adverse effects if the other drug is not used at all.

(xvi) Another drug attribute is the extent to which compliance with a treatment regime regarding administration (i.e., the physician's instructions or other appropriate guidelines) will affect treatment outcomes. Characteristics within this attribute of individual drugs will usually fall within the range of (a) drugs for which compliance with a specific treatment regime is critical for a positive treatment outcome to (b) drugs for which a wide range of treatment regimes are likely to result in a positive treatment outcome. Another possible characteristic within this drug attribute are for drugs for which a positive treatment outcome is less critical (e.g., drugs used for cosmetic purposes).

(xvii) Another drug attribute, which is related to compliance with a treatment regime (item (xvi), immediately above), is the extent to which patient support is necessary to insure compliance with the treatment regime. For example, some drugs may be characterized by unpleasant adverse effects (which may or may not be severe), which may cause patients to terminate the respective treatment regimes before completion, and other drugs may be characterized by a significant lag time between commencement of the treatment regime and observable positive effects. In each case, the patient may be not be motivated to fully comply with the prescribed treatment regime. Thus, such drugs may have the characteristic of requiring significant patient support to insure patient compliance with the entire treatment regime. In contrast, other drugs characterized, for example, by minimal side effects and/or as providing early, noticeable improvements, may be characterized as requiring little or no patient support to insure the patient will continue the prescribed treatment regime through completion.

(xviii) "Conditions a drug may be used to treat" is another drug attribute. Those skilled in the art will understand that a drug may be used to treat more than one condition and that "condition" can be variously defined (e.g., "condition" may be used in a medically narrow sense or in a broader sense as including, for example, diseases and syndromes). For example, a "condition" could be characterized as "cancer," "lung cancer," "non-small cell lung cancer," or as "adenocarcinoma," depending, for example, upon the desired level of specificity. The specific indication(s) of a drug for which FDA (United States Food and Drug Administration) approval has been granted can further characterize a drug with respect to this attribute.

(xix) Certain attributes of the conditions drugs are used to treat may also be drug attributes for purposes of the present invention. Thus, "level of clinical expertise required to understand conditions a drug may be used to treat" is a drug attribute, and characteristics of this attribute may include (a) the condition the drug is used to treat is generally well understood by most health care providers (e.g., hepatitis B), (b) the condition the drug is used to treat is generally well understood only by those health care providers who have some level of special training and/or experience in that condition (e.g., hepatitis C, multiple sclerosis, HIV, and growth deficiency), and (c) the condition the drug is used to treat is generally well understood only by a limited group of health care providers with a particular expertise in that condition (e.g., hemophilia, Hunter Syndrome, and pulmonary arterial hypertension).

(xx) "Pervasiveness (prevalence) of conditions a drug may be used to treat" is a drug attribute, which may be characterized by use of the drug to treat (a) a common condition (e.g., one that is sufficiently prevalent such that care typically could be provided by a health care provider with general expertise), (b) a somewhat less prevalent condition (e.g., one usually treated by a specialist, but one for which specialists are somewhat readily available), or (c) a rare condition (e.g., one usually treated by a specialist and for which there are few specialists). Because a drug may be used for treating more than one condition, a drug could be characterized both as a drug used to treat a common condition and one used to treat a rare condition. Alternatively, if a drug is used to treat a rare condition, it could be characterized as a drug used to treat a rare condition even if the drug might also be used to treat a more common condition. Related to this attribute may be the frequency of new diagnoses of the conditions a drug is used to treat. In many cases, the prevalence of a condition (i.e., the number of patients living with the condition during a given time period) and the frequency of new diagnoses of the condition (i.e., the number of patients newly diagnosed with a condition during a given time period) may be similar; however, this may not be the case with all conditions. For example, certain chronic conditions might be relatively more common with respect to the number of patients living with the condition but somewhat rarer with respect to new diagnoses.

(xxi) Conditions drugs are used to treat can be grouped into "therapy classes," and a drug may be characterized by, e.g., the therapy class or classes of the conditions a drug is used to treat. As with other drug attributes, there can be different definitions of "therapy class," e.g., depending on the desired level of specificity. In some instances, a therapy class may be defined by both the condition to be treated and the mode of administration. For example, therapy classes preferably include: age-related macular degeneration, allergic asthma, alpha-1 antiryspin deficiency, blood cell deficiency, cancer treated by injectable drugs and/or recently-introduced oral drugs, endocrine disorders, enzyme deficiency, growth deficiency, hemophilia, hepatitis C, HIV treated by injectable drugs, immune deficiency, infertility, inflammatory conditions, iron toxicity, multiple sclerosis, osteoporosis, pulmonary hypertension, respiratory conditions, RSV prevention, organ transplant treated by injectable drugs, and conditions treated by so-called "orphan drugs" (a term understood by those skilled in the art).

As will be apparent to one skilled in the art, the preceding list of drug attributes is representative and not exhaustive and the invention, its embodiments, and their utilization do not depend on the specific list and/or descriptions of attributes or characteristics. Thus, one or more of the above-described attributes may be used, one or more of the above-described characteristics for those attributes may be used, and/or one or more other attributes and/or characteristics may be used with or without one or more of the above-described attributes and/or characteristics.

As more fully discussed below, the step of the present invention of establishing which of the drug attributes are relatively more important for determining whether a drug is a specialty drug may result in a combination of what have been described above as multiple attributes into a single attribute (or vice versa) and/or a re-characterization of an attribute as, for example, one or more of the characteristics by which another attribute is defined (or vice versa). None of that has any adverse effect on the present invention or its advantages.

Establishing Relatively More Important Drug Attributes

In accordance with a method of the present invention for creating a tool for use in identifying which drugs are specialty drugs, certain drug attributes are established (i.e., identified, selected, etc.) as relatively more important and that can be done by a variety of means alone or in combination, which drug attributes established as relatively more important drug attributes are then used in a method of the invention for identifying which drugs are specialty drugs.

In a preferred embodiment, one or more individuals skilled in the pharmaceutical arts (e.g., a pharmacist, a physician, a nurse, or other person with sufficient knowledge of drugs and/or drug distribution to make a skilled determination) and with sufficient knowledge and/or understanding of the services provided by a specialty pharmacy and/or the availability of special services for drug distribution and/or delivery and/or special services for patient care (a "skilled individual") will select one or more relatively more important drug attributes based, at least in part, upon his or her understanding of the available services and a comparison of those available services to the drug attributes. Alternatively, or in combination with the above, establishment of relatively more important drug attributes can be made by taking into consideration services deemed (by one or more skilled individuals) to be desirably provided in connection with the provision of certain drugs. Thus, for example, a review of a drug attribute may result in a skilled individual determining that certain services would desirably be provided in connection with the provision of certain drugs. If such services could or should be provided by a specialty pharmacy, determination that such services would be desirable (and could be provided) may result in that drug attribute being selected as a relatively more important drug attribute. Selection (establishment) of the relatively more important drug attributes may be regional. For example, some aspects of or related to patient care may be more important in rural areas (or, more generally, areas underserved by health care providers) than areas more well-served by health care providers.

Establishing relatively more important drug attributes can be made by a single skilled individual and/or by more than one skilled individual. A group of skilled individuals may work together to establish a set of relatively more important drug attributes by consensus. Selections of relatively more important drug attributes can be made by a group of skilled individuals and those selections can be used to establish a set of relatively more important drug attributes. For example, a relatively more important drug attribute could be defined as one selected as such by a specified percentage of a group of skilled individuals, e.g., at least 10% of the skilled individuals, at least 25% of the skilled individuals, at least 50% of the skilled individuals, or at least 75% of the skilled individuals.

Technology could be used in the establishment of relatively more important drug attributes, for example, to identify trends in the characteristics of drugs currently dispensed via a specialty pharmacy. This information could then be used, for example, to narrow the list of drug attributes to be considered by one or more skilled individuals as they establish relatively more important drug attributes. Alternatively, automated means (e.g., a programmed general purpose computer or a special purpose computer) could be used alone in combination with other means to establish the relatively more important drug attributes, e.g., based on quantifiable criteria, for example, criteria concerning cost of the drug in question, temperature range for its delivery and storage, pervasiveness of the condition for which it is usually prescribed, number of specialists (e.g., Board Certified), who are likely to be familiar with the condition for which the drug in question is usually prescribed, compared to the number of general practitioners, who are not likely to be familiar with that condition, and relative effect each of the attributes likely has on patient care or overall cost to a third party (e.g., patient, PBM) or some other criterion.

Preferably the following drug attributes are established as relatively more important drug attributes: (a) the level of patient training required for the route of administration that is not generally available to patients via traditional health care providers, (b) the uniqueness of the route of administration, (c) cost, (d) the means of preparation of a drug for delivery to the patient, (e) the means of preparation of a drug for administration to the patient, (f) storage requirements, (g) handling requirements, (h) delivery requirements, (i) potential toxicity, (j) the level of incidence and/or severity of adverse reactions, (k) the extent to which patient support is necessary to insure compliance with a treatment regime, (l) the level of clinical expertise required to understand a condition a drug will be used to treat, and (m) the pervasiveness of a condition a drug will be used to treat.

Relatively more important drug attributes can be established at a "higher level" or at a "lower level" than as previously described, e.g., as part of identifying drug attributes, as part of establishing the relatively more important drug attributes, and/or as part of establishing criteria to determine an attribute value for a drug with respect to each relatively more important drug attribute. This is further described through exemplification, as follows.

In a preferred embodiment, one or more of the following "higher level" attributes are used and most preferably all are used together: (1) a first relatively more preferred drug attribute combines (a) the level of clinical expertise required to understand a condition a drug will be used to treat and (b) and the pervasiveness of a condition a drug will be used to treat into a single attribute, which can be identified as the level of specialized clinical services required to support patient understanding and/or self-management of a condition a drug will be used to treat; (2) a second relatively more important drug attribute combines (c) the level of patient training required for the route of administration of a drug that is not generally available to patients via traditional health care providers and (d) the uniqueness of the route of administration of a drug into a single drug attribute grouping characteristics related to the level of specialized administration of the drug; (3) a third relatively more important drug attribute combines (e) potential toxicity and (f) the level of incidence and/or severity of adverse reactions into an attribute of level of specialized clinical monitoring required due to drug toxicity and/or pervasiveness of adverse reactions; (4) a fourth relatively more important attribute is the extent to which patient support is necessary to insure compliance with a treatment regime; (5) a fifth relatively more important drug attribute concerns product handling, preparation, and storage requirements, which attribute combines the above-described attributes of (g) the means of preparation for delivery to the patient, (h) the means of preparation for administration to the patient, (i) storage requirements, (j) handling requirements, and (k) delivery requirements; (6) a sixth relatively more important drug attribute concerns distribution channels; (7) a seventh relatively more important drug attribute is cost; and (8) an eighth relatively more important drug attribute is the therapy class of conditions a drug may be used to treat.

With respect to establishing relatively more important drug attributes at a lower level, establishment of those attributes could occur at the level of what have been referred to herein as "characteristics." That might result in the following set of relatively more important drug attributes: (1) highly specialized clinical expertise required to support patient understanding and/or self-management of the condition to be treated by the drug, (2) the condition to be treated by the drug is rare, (3) very intensive patient training is required for administration of drug, (4) highly specialized means of administering the drug are required, (5) the drug is highly toxic, (6) there are common adverse reactions to the drug, (7) compliance assistance is necessary to insure compliance with the treatment regime, (8) specialized handling, preparation, and/or storage are required for the drug, and (9) the drug is available only via limited distribution channels.

In some preferred embodiments, the relatively more important drug attributes include one or more of the following: (a) the level of specialized clinical services required to support patient understanding and/or self-management of the indicated condition, (b) the level of specialized administration of the drug, (c) the level of specialized clinical monitoring required due to drug toxicity and/or pervasiveness of adverse reactions, (d) the extent to which patient support is necessary to insure compliance with a treatment regime, (e) the product handling, preparation, and storage requirements, and (f) the breadth of distribution channels.

In some preferred embodiments, the relatively more important drug attributes comprise at least three of the following: (i) route of administration; (ii) targeted disease or condition; (iii) possible adverse drug reactions; (iv) risk of toxicity; (v) cost; (vi) extent to which patient support is necessary to insure compliance with a treatment regime; (vii) handling and/or storage requirements; and (viii) preparation requirements.

Thus, it will be understood by one skilled in the art that a drug attribute can be identified in any way and at any level so long as an "attribute" concerns or refers to aspects (and/or categories of aspects) of drugs and/or their use and/or the conditions treated by them and/or their storage and/or their distribution and/or their preparation, including by way of example and not by way of limitation the twenty-one items identified above (items numbered (i) to (xxi): physical attributes, route of administering, level of patient training required to understand and/or implement the route of administration, etc.) and various combinations of them.

Determining the "Attribute Value" of a Drug with Respect to Each of the Relatively More Important Drug Attributes Embodiments of the present invention provide methods of identifying drugs as specialty drugs that are more objective than known methods. The methods of this invention are facilitated by establishing criteria to determine an attribute value for a drug with respect to each relatively more important drug attribute. These criteria give individuals who, or technological means that, are to determine whether a drug is a specialty drug clear guidance as to how to make this determination. With known methods, a skilled individual determining whether a drug was a specialty drug would in essence just answer "yes" or "no" based upon his or her understanding of the definition of "specialty drug," with no particular guidance on how to consider and balance the various parts of that definition. Under the methods of the present invention, however, an individual or technological means making the determination is provided with a specific set of relatively more important drug attributes (which makes it clear which drug attributes are to be considered) and with specific criteria for evaluating a drug with respect to each such attribute. That evaluation then dictates an "attribute value" for that drug with respect to that relatively more important drug attribute, thereby providing a more objective determination of whether a drug is a specialty drug.

Embodiments of the invention that make possible these more objective determinations provide the further benefit of reducing inconsistencies between the determinations made by different individuals or technological means. That in turn may reduce or eliminate the level of review previously required for a designation of a drug as a specialty drug or, conversely, for the designation of a drug as a non-specialty drug. Furthermore, customers of a PBM, pharmacy, manufacturer, or other entity responsible for distributing, dispensing, and/or administering drugs that have been identified as specialty drugs using a method of the present invention can more easily understand why a drug has been characterized as a specialty drug.

Establishing the criteria for determining attribute values will often and most conveniently occur concomitantly with and by the same means as establishing which of the drug attributes are the relatively more important ones, e.g., by a single skilled individual, by a group of skilled individuals (by consensus or otherwise), and/or via the use of appropriate technology.

The criteria used to determine the attribute value of a drug with respect to a relatively more important drug attribute can take a wide variety of forms, as can the form of the attribute value ultimately assigned to a drug with respect to a particular relatively more important drug attribute. The same form of criteria, and/or the same form of attribute value, need not be used for each of the relatively more important drug attributes.

Criteria for determining an attribute value for each relatively more important drug attribute preferably concern characteristics of drugs (or ranges of characteristics of drugs) for each such particular drug attribute, along with one or more values (numeric or otherwise) corresponding to one or more of such characteristics (or ranges of characteristics). Thus, through use of the established valuation criteria, a drug's attribute value with respect to a given relatively more important drug attribute can be established as the value associated with such characteristic (or range of characteristics).

The attribute value may take the form of a score. While numerical scoring is generally well-understood and, therefore, is preferred, it will be understood by one skilled in the art that other forms of scoring may be used to establish the attribute value of a drug. For example, letters or other symbols could be used to identify where within the range of characteristics by which an attribute is defined a particular drug lies.

The form of the criteria for assessing the attribute value of a drug with respect to a particular relatively more important drug attribute may depend upon the level at which the attribute is defined. For example, where the relatively more important drug attributes are identified at the characteristic level, the attribute value of a drug, with respect to one or more of the identified relatively more important drug attributes, may be a value that designates a particular relatively more important drug attribute as present ("yes"; "1") or not present ("no"; "0"). Another possibility is to establish scores to indicate whether one or more skilled individuals who may be asked to determine whether a particular drug is a specialty drug "strongly agree," "somewhat agree," or "do not agree" that a drug to be evaluated has the characteristics (e.g., high toxicity) of each of the drug attributes being evaluated (e.g., potential toxicity).

In FIG. 1, which shows tool 10 of the present invention in tabular or chart form, six drug attributes (column 12) are being used. Attributes A, B, and C relate to "Care," attributes D and E related to "Service," and attribute F relates to "Access" (if drug attributes were being established at a higher level than drug attributes A through F, the drug attributes might be called "level of care," "level of service," and "access"). Also shown are characteristics (column 14) for each attribute (i.e., the criteria for categorizing a drug with respect to each attribute), the corresponding attribute values (column 16), and examples to guide one skilled in the art (or technological means, e.g., a computer) when determining which characteristic the drug in question has (column 18).

Providing such examples is optional but desirable because doing so promotes objectivity and/or consistency by helping to resolve possible ambiguities about how a particular drug should be characterized.

For drug attribute A (concerning the level of specialized clinical services required to support patient understanding and/or self-management of the condition the drug is used to treat), there are three mutually exclusive characteristics (or categories), each with a corresponding score (attribute value). A score of 2 points is awarded for having the characteristic of requiring highly specialized clinical expertise to support patient understanding of a condition the drug in question is used to treat and the condition being rare. Examples include hemophilia and pulmonary arterial hypertension. A score of 1 point is awarded for having the characteristic of either requiring specialized clinical expertise to support patient understanding of a condition the drug in question is used to treat or the condition being rare, but not both. Examples include Hepatitis C, multiple sclerosis (MS), and cancer. A score of zero is awarded for having the characteristics of requiring only general clinical expertise to support patient understanding of a condition the drug in question is used to treat and the condition not being rare. An example is Hepatitis B immune globulin.

For drug attribute B (concerning the level of specialized requirements for intensive patient training specific to administration of the drug or specialized requirements for administration of the drug), there are three mutually exclusive characteristics. A score of 2 is awarded for having the characteristic of having a route of administration that requires very intensive patient training or having highly specialized requirements if administration is by a healthcare professional. Examples include the drugs sold under the marks Vivaglobin® and Avastin®. A score of 1 is awarded for having the characteristic of either having a route of administration that requires moderately intensive patient training or that has moderately specialized requirements. An example is the drug sold under the mark Ventavis®. A score of zero is awarded for having the characteristic of having a route of administration that is not specialized or that requires only average patient training. An example is the drug sold under the mark Gleevec® (oral).

For drug attribute C (concerning the level of specialized requirements for clinical monitoring required because of drug toxicity and to monitor for therapeutic effect), there are three mutually exclusive characteristics. A score of 2 is awarded for having the characteristic of requiring very intensive clinical monitoring because of high toxicity and/or common severe adverse reactions. An example is the drug sold under the mark Flolan®. A score of 1 is awarded for having the characteristic of requiring moderately intensive clinical monitoring because of moderate toxicity and/or less common adverse reactions. An example is the drug sold under the mark Revlimid®. A score of zero is awarded for having the characteristic of requiring only an average level of clinical monitoring. An example is the drug sold under the mark Gleevec® (oral).

For drug attribute D (concerning the extent of specialized requirements for compliance assistance by the patient to facilitate therapeutic goals), there are three mutually exclusive characteristics. A score of 2 is awarded for having the characteristic of compliance being necessary to facilitate therapeutic goals. An example is the drug sold under the mark Flolan®. A score of 1 is awarded for having the characteristic of compliance being recommended to facilitate therapeutic goals. An example is the drug sold under the mark Rebif®. A score of zero is awarded for having the characteristic of compliance being optional to facilitate therapeutic goals. An example is the drug sold under the mark Botox®.

For drug attribute E (concerning the extent of specialized requirements for handling, preparation, and storage of the drug), there are three mutually exclusive characteristics. A score of 2 is awarded for having the characteristic of having highly specialized requirements. An example is the drug sold under the mark Ellence® (intravenous). A score of 1 is awarded for having the characteristic of having moderately specialized requirements. An example is the drug sold under the mark Avonex®. A score of zero is awarded for having the characteristic of not having specialized requirements. An example is the drug sold under the mark Revatio®.

For drug attribute F (concerning distribution channels for the drug), there are two mutually exclusive characteristics. For reasons explained below and as shown in box 20 of FIG. 1, a score of from zero to 10 is awarded for having the characteristic of being available only through limited distribution channels, e.g., if the pharmacy for which identification of drugs as specialty drugs is being made is an exclusive distributor of the drug in question. An example is the drug sold under the mark Iressa®. A score of zero is awarded for having the characteristic of being available through open distribution channels, e.g., if the pharmacy for which identification of drugs as specialty drugs is being made is not an exclusive distributor of the drug in question. An example is the drug sold under the mark Revatio®.

In this context, "exclusive" does not necessarily mean there are no other pharmacies designated by the manufacturer (or other entity that controls distribution and/or availability of a drug) to be distributors of the drug. Thus, "exclusive" can refer to situations in which a manufacturer (or other entity that controls distribution and/or availability of a drug) has limited the distribution of the drug to only those pharmacies that will offer special services in connection with dispensing and/or administering the drug and/or in connection with providing support to a patient to whom the drug is administered and/or to the caregivers of that patient.

The reason the score in box 20 is from zero to 10 is as follows. In the embodiment shown, if the pharmacy for which the determination is being made as to whether a drug is a specialty drug has the above-described "exclusive" arrangement, the drug will automatically be deemed to be a specialty drug. The total for attributes A, B, C, D, and E for a given drug is anywhere from zero to 10. Thus, because according to this embodiment, a total of 10 points is needed to be deemed a specialty drug, the score for box 20 will be that number of points needed to bring the total for all of the attributes, i.e., A through E plus F, to 10.

With the tool of FIG. 1, the characteristics of the drug in question are compared to the two or three characteristics identified for each relatively more important drug attributes A, B, C, D, E, and F and for each attribute, the value associated with the characteristic of the drug (i.e., the score for the category into which the drug falls) is assigned to the drug as its attribute value for that attribute, after which the scores for all six attributes (A to F) are totaled.

As noted above, cost (which is not an attribute listed in FIG. 1) is desirably a relatively more important drug attribute, and cost can be defined in different ways. Preferably, "cost" is a drug's AWP (average wholesale price) or a fraction of the AWP for an average 30-day dosage and a drug may be characterized by its falling within a cost range. For example, three ranges of cost could be established as (i) less than $500 for a 30-day period, (ii) from $500 to $1000 per 30-day period, and (iii) more than $1000 per 30-day period. A value (e.g., "low," "medium," or "high") is desirably associated with each established cost range. Preferably, the "attribute value" associated with each cost range is the cost range itself into which the drug falls.

Preferably, the therapy class a condition a drug may be used to treat is a relatively more important drug attribute (which attribute is also not listed in FIG. 1), therapy classes are identified as characteristics to determine the attribute value of a drug for this attribute, and the attribute value is simply the identification of that therapy class.

Characteristics reasonably related to each attribute that allow for meaningfully differentiating different drugs from one another with respect to that attribute (i.e., categorizing the drugs with respect to that attribute) will be apparent to those skilled in the art. In FIG. 1, the characteristics set forth for each attribute are preferred but exemplary and not exhaustive.

As will be apparent to one skilled in the art, some or all of the attributes and/or characteristics and/or attribute values will likely have different degrees of importance for determining whether a drug is a specialty drug. For example, not all drug attributes are relatively more important drug attributes and for a given attribute, not all possible characteristics are of equal significance (see, e.g., column 16 of FIG. 1). Relative significance is further discussed below.

Determining the "Overall Value" of a Drug and Using that "Overall Value" to Determine Whether a Drug is a Specialty Drug The next steps in a preferred method of this invention for determining whether a drug is a specialty drug are to determine the "overall value" of the drug, based on the attribute values of the drug, and then to determine whether a drug is a specialty drug, based on the overall value of the drug. In a preferred method of this invention for creating a tool for use in making the preceding determinations, the corresponding next steps are to establish procedures (i.e., means, methods, criteria) for making those determinations.

Determining the overall value of a drug will include, at least in part, further analysis and/or manipulation of the previously-determined individual attribute values. For example, specific instructions may be provided regarding how the relatively more important drug attributes and the individual attribute values are to be considered in making a determination of whether a drug is a specialty drug. Having clear instructions for doing so, which can be inspected by third parties (e.g., PBMs and their customers), helps provide a more objective and more understandable method of identifying specialty drugs and moves the present invention still further away from the known yes-or-no subjective methods. Such instructions are readily understood and can be easily implemented by an individual or by technological means using a method and/or tool of the invention.

The method for determining the overall value from the several individual attribute values, the resultant overall value itself, and the criteria for establishing that method will depend at least in part upon the method used to determine the attribute values. For example, when numerical or other symbolic scores are the attribute values of a drug for two or more drug attributes, it may be appropriate to mathematically manipulate, combine, or otherwise consider together (collectively "mathematically combine"), e.g., arithmetically, graphically, algebraically, or otherwise, a drug's different attribute values to establish part or all of a drug's overall value. Thus, one part or all of the overall value of a drug could simply be the sum of some or all of those attribute values, i.e., part or all of the drug's overall value would result from adding designated attribute values. Some or all of the attribute values could be weighted (e.g., multiplied by numbers less than or greater than 1) and the resulting weighted attribute values added. As another example, some or all of the attribute values could be multiplied by each other, with or without first weighting them with appropriate factors. As still another example, values of a drug with respect to one or more relatively important drug attributes could be plotted on a graph, with the overall value of a drug then based upon the plotted positions (e.g., using area-under-the-curve values). If letter scores are used for one or more attribute values, the overall value could include identification of the number of each letter score awarded to a particular drug. Thus, if possible attribute values are "A," "B," and "C," a particular drug's overall value could be, e.g., three As, two Bs, and one C (assuming there are six relatively more important drug attributes for which such a letter score is awarded as an attribute value). In this case, rules would also be established for determining what the minimal A, B, and C totals are for then classifying a drug as a specialty drug. For those embodiments of the present invention in which the overall value of a drug includes a numerical component, that component of a drug's overall value need not be a single numerical value but instead could be a numerical range.

Another possibility when some or all of the relatively more important drug attributes are established at the level of drug characteristics is that a drug's attribute value with respect to each such drug attribute may be "Yes" if the attribute (characteristic) is present and "No" if it is not. In that case, with, e.g., ten attributes, the possible overall value would run from zero Yeses to ten Yeses and those could be divided into, e.g., three ranges: (i) zero to three "Yeses," (ii) four to seven "Yeses," and (iii) eight to ten "Yeses." In that case, drugs whose "Yes" totals put them in the third category (range) could be deemed to be specialty drugs, regardless of cost, drugs whose "Yes" totals put them in the second category (range) could be deemed to be specialty drugs only if their cost were above some threshold value, and drugs in the first category could be deemed to be specialty drugs only if their cost were above some even higher threshold value.

As indicated above, a drug's overall value may have more than one component, particularly if not all attribute values take the same form. For example, one part of the overall value may be numerical (e.g., the sum of certain designated attribute values where each is scored zero, 1, or 2) and another part of the overall value may non-numeric or numeric but kept separate from the first part (e.g., the price of the drug for a 30-day supply).

As an example, in a preferred embodiment of the present invention, the overall value for a drug comprises three elements ("specialty points," cost, and therapy class), and the methods used to establish them are as follows.

(1) "Specialty Points": The drug is assessed with respect to the established attributes using the range of possible characteristics for each attribute, and the attribute value for each attribute is determined (see, e.g., preceding discussion of FIG. 1). The individual attribute values are then added, and the total is denominated the drug's "specialty points." Preferably, the attributes concern: (a) the level of specialized clinical services required to support patient understanding and/or self-management of the indicated condition, (b) the level of specialized administration of the drug, (c) the level of specialized clinical monitoring required due to drug toxicity and/or pervasiveness of adverse reactions, (d) the extent to which patient support is necessary to insure compliance with a treatment regime, (e) the product handling, preparation, and storage requirements, and (f) the breadth of distribution channels.

(2) Cost: The drug's cost is located in one of the ranges established for the attribute of cost (e.g., less than $500 for a 30-day supply, from $500 to $1000 for a 30-day supply, and greater than $1000 for a 30-day supply), and that range is the attribute value of the attribute of cost.

(3) Therapy Class: The condition for which the drug is typically prescribed is located in one of the groups established for the attribute of therapy class, and that class is the attribute value of the attribute of therapy class.

Regardless of how the overall value is determined and regardless of its form, e.g., a single or group of characters, symbols, indicators, or other values of the same or different types, the overall value is assessed using established procedures (including criteria) to determine whether the drug in question is a specialty drug.

Criteria for determining whether a drug is a specialty drug, based on the overall value of the drug, may include one or more threshold values for comparison with a drug's overall value or a component of the drug's overall value. Different types of criteria may be provided for different parts or aspects of a drug's overall value. In some cases, determination of whether a drug is a specialty drug may be based solely on some (and not all) aspects of a drug's overall value; however, even in this case, the determination of whether a drug is a specialty drug is still considered to be based on the overall value of the drug.

The threshold values can be established by one or more of the methods described above with respect to establishment of the relatively more important drug attributes, e.g., by a single skilled individual, by a group of skilled individuals (by consensus or otherwise), and/or by use of appropriate technology. If, for example, an overall value consists of two parts, there can be more than one threshold value for one of the parts depending on the level of the other part. Similarly, an overall value consisting of three or more parts could have multiple thresholds for two or more of the parts depending on the levels of one or more other parts.

For example, in a preferred embodiment of the invention, in which the overall value includes aspects of specialty points and a cost range, criteria for determining whether a drug is a specialty drug, based on its overall value may include: (1) a first numerical threshold value that is based on the range of possible specialty points and that is used when the drug's cost is in a first cost range, (2) a second numerical threshold value that is based on the range of possible specialty points and that is used when the drug's cost is in a second cost range, and (3) a third numerical threshold value that is based on the range of possible specialty points and that is used when the drug's cost is in a third cost range.

In that case, when using a tool or method of the present invention, a user may first determine a drug's attribute value with respect to each relatively more important drug attribute and then determine the total number of specialty points. The user than identifies the threshold value that is associated with the cost range into which the cost of the drug falls and if the actual number of specialty points meets or exceeds that threshold, the drug is denominated a specialty drug.

As a more specific example, when using specialty points and cost to determine whether a drug is a specialty drug, a first threshold value of 8 specialty points may be designated for drugs in a first cost range of less than $500 per 30-day period, a second threshold value of 5 specialty points may be designated for drugs in a second cost range of from $500 to $1000 per 30-day period, and a third threshold value of zero specialty points may be designated for drugs in a third cost range of more than $1000 per 30-day period. In such a case, a drug would then be denominated (i.e., determined to be) a specialty drug if (i) it is in the first cost range (less than $500 per 30-day period) and it has at least 8 specialty points or (ii) it is in the second cost range (from $500 to $1000 per 30-day period) and it has at least 5 specialty points or (iii) it is in the third cost range (more than $1000 per 30-day period), regardless of how many specialty points it has. In other words, although the total number of specialty points is part of a drug's overall value, if the drug's cost puts the drug in the third cost range, the drug's number of specialty points is irrelevant to the determination and the drug will be denominated a specialty drug.

Determining Whether a Therapy Class of Drugs are Specialty Drugs. In a preferred embodiment of the invention, the ultimate determination is not whether an individual drug is a specialty drug, but whether all drugs within a therapy class are specialty drugs. One benefit of this embodiment is that a patient who may be receiving more than one drug within a therapy class can then receive all of those drugs from the same source (i.e., a specialty pharmacy) even if only one but not all of the patient's drugs meet the criteria for being denominated specialty drugs. In this embodiment, a relatively more important drug attribute is therapy class and, thus, an aspect (part) of a drug's overall value is its therapy class. Determining whether a drug is a specialty drug based on its overall value will then (i) include considering that aspect of the drug's overall value that is its therapy class and (ii) preferably include comparing or otherwise analyzing other aspects of the overall values of drugs within that therapy class as a group to determine whether drugs within that therapy class are specialty drugs.

Thus, in a preferred embodiment for determining whether drugs within a therapy class are specialty drugs, certain aspects of the overall values of the drugs may be averaged to yield a "therapy class overall value," which is then used to make the determination, e.g., using the criteria established for that purpose, as discussed above. Of course, just as the overall value of a drug can have a variety of forms and have more than one aspect (part), the therapy class overall value can have a variety of forms and more than one aspect (part). Although unweighted averaging (i.e., determining the mean average without weighing the overall value for any drug more than the overall value for any other drug) is preferred, a therapy class overall value may be obtained by any other method that results in a therapy class overall value that represents in a desired way the overall values of the drugs within that therapy class. For example, weighted mean average values could be used.

As an example, in an embodiment of the invention in which specialty points and cost (e.g., average wholesale price) are components of a drug's overall value, determination of whether a therapy class of drugs are specialty drugs could be made as follows.

(1) The attribute values of more than one drug within a therapy class are determined using a method of the present invention.

(2) The attribute values of those relatively more important drug attributes relevant for purposes of calculating the drug's specialty points are added or otherwise combined for each drug to determine this aspect of each drug's overall value (e.g., to produce a total number of specialty points for each drug).

(3) The points (e.g., specialty points) for the drugs within the therapy class are averaged, desirably using all or a reasonable (representative) sample of the drugs within that therapy class.

(4) The costs of the drugs (i.e., that aspect of each drug's overall value that is its cost) within the therapy class are averaged for all of the drugs or for the same sample used in step (3).

(5) The average points (e.g., specialty points; step 3) and the average cost (step 4) of the drugs within the therapy class, which together comprise its "therapy class overall value," are used to make the determination (of whether drugs within the therapy class are specialty drugs), e.g., in the same ways discussed above for determining whether an individual drug is a specialty drug. For example, a first threshold specialty point value is designated for a first therapy class cost range, a second threshold specialty point value is designated for a second therapy class cost range, and a third threshold specialty point value is designated for a third therapy class cost range; the appropriate threshold specialty point value is selected according to which of the three cost ranges the therapy class average cost falls in; and the class average specialty point value is compared to that specialty point threshold value. If the class average specialty point value is at least as great as that threshold specialty point value, the class is deemed special and all of the drugs in that class are deemed to be specialty drugs.

Creating and Using a Tool of the Present Invention

As described herein, different aspects of the present invention concern (i) a method for determining whether one or more drugs are specialty drugs (including whether the drugs in a group, e.g., a therapy class, are specialty drugs), (ii) the tool used to make the determination, and (iii) a method for creating (establishing) the tool.

A more time-consuming or elaborate method of this invention for determining whether one or more drugs are specialty drugs includes the steps of: (1) establishing which of the set of drug attributes are relatively more important for determining whether a drug is a specialty drug; (2) establishing one or more procedures (including criteria) to determine an attribute value of a drug with respect to each relatively more important drug attribute; (3) establishing one or more procedures (including criteria) to determine the overall value of a drug based on the attribute values of that drug; (4) establishing one or more procedures (including criteria) to determine whether a drug is a specialty drug based on its overall value; (5) obtaining for a given drug its attribute value with respect to each of the relatively more important drug attributes using the procedures established by step (2); (6) obtaining for that drug its overall value based on its attribute values using the procedures established by step (3); and (7) determining whether the drug is a specialty drug based on the overall value using the procedures established by step (4).

Once steps (1) through (4) have been carried out, those steps need not (and preferably should not) be repeated for each drug being assessed (i.e., for which the determination is being made of whether it is a specialty drug). Thus, a shorter method of this invention for determining whether one or more drugs are specialty drugs includes the steps of: obtaining a pre-existing tool embodying the results (e.g., procedures) of steps (1) to (4), which tool may have been created by a third party or by the party who will carry out steps (5) to (7) or partially by each of those parties, and then using that tool to carry out steps (5) to (7) for one or more drugs (including for a group of drugs, e.g., a therapy class of drugs). Of course, the tool preferably is examined from time to time to determine whether it continues to embody appropriate methodology (including criteria) and, if not, to revise the tool by repeating one or more of steps (1) to (4).

A tool used in making the determination (of whether one or more drugs are specialty drugs) may comprise and/or rely on one or more procedures (sets of instructions) and/or lists, databases, spreadsheets, or other arrangements of data that set forth or otherwise concern one or more of the following: (a) a set of relatively more important drug attributes, (b) one or more procedures (including criteria) to determine an attribute value of a drug with respect to each relatively more important drug attribute, (c) one or more procedures (including criteria) to determine the overall value (or part of the overall value) of a drug based on the attribute values of that drug, and/or (d) one or more procedures (including criteria) to determine whether a drug is a specialty drug based on its overall value.

As indicated, a tool may comprise and/or rely on one or more procedures (embodied, for example, in sets of instructions) and/or lists, databases, spreadsheets, or other arrangements of data that set forth or otherwise concern less than all of items (a) to (d). For example, in the tool illustrated in FIG. 1, the tool (i) lists the relatively more important drug attributes relevant for purposes of calculating a drug's specialty points, (ii) implicitly contains a procedure to determine the attribute value of a drug with respect to each such relatively more important drug attribute (namely, by listing two or three mutually exclusive characteristics for each attribute and a point value associated with each characteristic), and (iii) implicitly contains a procedure to determine part of the overall value of a drug (i.e., specialty points) based on the attribute values of a drug (namely, by listing points for each mutually exclusive characteristic and in box 20 of FIG. 1 indicating that having the characteristic of being available only through a limited distribution channel corresponds to a sufficient number of points to bring the total number of points to 10). The tool of FIG. 1 does not explicitly contain a procedure to carry out step (d). The tool of FIG. 1 may conveniently be embodied in technology (e.g., a computer program) and in technology (e.g., a computer program) that incorporates step (d).

As another example, a tool of this invention could embody just the procedures (or even just the criteria) for establishing which of the set of drug attributes are relatively more important for determining whether a drug is a specialty drug (item (a)).

As used herein, "procedures" should be broadly understood to include methods, processes, techniques, schemes, algorithms, as well as the criteria embedded or used in or with any of the foregoing. As used herein, "criteria" should be broadly understood to include standards, rules, measures, and the like. Once criteria have been established, e.g., for determining an attribute value of a drug with respect to a relatively more important drug attribute, there may be different ways for carrying out the procedure of making that determination using those criteria. Thus, the criteria that have been established will be used in the methods and tools of this invention even if the particular procedures used are not the same as those that may have been established.

A party making a determination of whether a drug is a specialty drug in accordance with this invention will be using a tool of this invention and, as indicated above, that tool may have been created by that party or by a third party or partially by each. Thus, the term "obtaining a tool for use in identifying specialty drugs" and the like should be broadly understood and include and/or refer to situations where the party making the determination has created the tool and then will be using it, as well as to situations where the party making the determination will be using a tool created by third party, as well as to situations where part of the tool has been created by the party using it and part of the tool has been created by a third party. In each case, the party making the determination is obtaining some or all of a tool for use in identifying specialty drugs before making the determination. All aspects (parts) of the tool will usually be pre-existing by the time its use is commenced, although in some cases only parts of it may be pre-existing (e.g., the set of the attributes deemed relatively more important for determining whether a drug is a specialty drug and the one or more criteria for determining the attribute value of a drug for each of the relatively more important drug attributes), those parts used, and then other aspects (parts) of the tool established (e.g., the one or more criteria for determining the overall value for a drug based on the attribute values and/or the one or more criteria for determining whether a drug is a specialty drug based on the overall value).

As indicated, some or all of the tool of this invention may conveniently be embodied in one or more computer programs (e.g., software, hardware, or firmware) or other technological means, which may identify for users some or all of the relatively more important drug attributes and identify and/or embody the procedures to determine an attribute value with respect to each such attribute. The tool could optionally permit a user to input information regarding particular drugs to facilitate some or all of the procedures to be used to determine attribute values (e.g., current average wholesale cost data) at the time one or more drugs are to be assessed for denomination as specialty drugs (e.g., cost data). The software could calculate a drug's attribute values, its overall value, and designate a drug as a specialty drug or as a non-specialty drug in accordance with a method of the invention.

Similarly, some or all of the method for making a tool of this invention may conveniently be embodied in one or more computer programs (e.g., software, hardware, or firmware) or other technological means. For example, programs or other technological means may be used to identify or to help identify which of the drug attributes are relatively more important drug attributes, and/or identify or to help identify which criteria are best used for determining the attribute value of a drug for each of the relatively more important drug attributes, and/or to identify or to help identify which criteria are best used for determining the overall value of a drug based on the attribute values for that drug, and/or to identify or to help identify which criteria are best used for determining whether a drug is a specialty drug based on the overall value of the drug.

Broadly speaking, after determining, being told, or otherwise obtaining a tool indicating which drug attributes are considered relatively more important, a user selects (or is given) a drug to evaluate, determines the characteristic of that drug with respect to each relatively more important drug attributes, assigns an attribute value to that drug based on the characteristics of that drug, determines the overall value of the drug from the various attribute values, and then determines whether the overall value puts the drug in the category of specialty drugs. Again, each of the steps may be carried out by technological means such as a computer.

Using a tool and method of the invention, as represented in FIG. 1, the drug Epogen® may be assigned an attribute value of 1 for drug attribute A (concerning level of specialized requirements for clinical services) because the drug is used to treat a complex condition; assigned an attribute value of 2 for drug attribute B (concerning the level of specialized requirements for intensive patient training specific to administration of the drug or specialized requirements for administration of the drug) because the drug is administered subcutaneously or intravenously and/or requires frequent shots during the course of treatment to determine proper dosage; assigned an attribute value of 2 for drug attribute C (concerning level of specialized clinical monitoring required because of drug toxicity and/or adverse reactions) because with the drug there are often relatively severe adverse reactions; assigned an attribute value of 1 for drug attribute D (concerning specialized requirements for compliance to facilitate therapeutic goals) because continued long-term compliance with the physician's instructions is recommended to facilitate therapeutic goals; assigned an attribute value of 1 for drug attribute E (concerning handling, preparation, and storage requirements) because the drug requires refrigeration and cannot be subjected to temperature extremes; and assigned an attribute value of zero for drug attribute F (concerning distribution channels) because the drug is available through an open distribution channel. The drug may also be assigned an attribute value concerning cost of the range of $500 to $1,000 because the drug's cost for a 30-day period falls within that range.

The attribute values obtained in steps A through F are then added to determine one aspect of the drug's overall value, resulting in a total number of specialty points of 7 (1+2+2+1+1+0). In this example, there are three cost ranges and each has a different threshold value associated with that range. Thus, drugs having a cost falling within the range of $500 to $1000 per 30-day period require a minimum threshold value of 5 specialty points to be denominated specialty drugs. Because Epogen® has 7 specialty points, using the above-described tool and method of this invention results in Epogen® being denominated a specialty drug.

In trials, tools and methods of the present invention have proved useful in both re-evaluating drugs that known methods identified as specialty drugs and in evaluating new drugs to determine whether they should or should not be identified specialty drugs. The re-evaluation indicated that the known method failed to identify as specialty drugs substances that should have been so identified and identified as specialty drugs substances that should not have been so identified (in other words, the known method produced both false positives and false negatives as judged from the perspective of tools and methods of the present invention).

It will be understood by one of ordinary skill in the art that while a drug may be designated as a specialty drug using a tool and/or method of the present invention, that drug may, in certain circumstances, nevertheless be dispensed other than via a specialty pharmacy. For example, in trials of a method and tool of the present invention, certain drugs that would otherwise have been determined to be specialty drugs using a tool and method of this invention were, nevertheless, not denominated as specialty drugs because they are "stat" drugs, i.e., the need for those drugs by a patient may be immediate, making the potentially more limited distribution via a specialty pharmacy less desirable. Of course, one drug attribute is the likelihood that a patient will require the drug immediately (where "immediate" might be within a defined period of time, e.g., 12 hours or 24 hours). Characteristics of drugs within this attribute could include "very likely," "less likely," and "not at all likely." Therefore, another manner of addressing the desirability of not designating "stat" drugs to be specialty drugs would be to include that attribute as a relatively more important drug attribute, establish criteria to evaluate a drug to determine its attribute value with respect to this relatively more important drug attribute, and include within the criteria for establishing a drug's overall value an evaluation, weighing, and/or other consideration of possible attribute values of this relatively more important drug attribute such that, e.g., drugs deemed "very likely" to be immediately required by a patient are deemed not to be specialty drugs regardless of the other attribute values the drug otherwise has.

The terms "first," "second," "third," "fourth," and the like in the description and in the claims, if any, are used for distinguishing between similar elements and not necessarily for describing a particular sequential or chronological order. It is to be understood that under appropriate circumstances the embodiments of the invention described herein are capable of operation in sequences other than those illustrated or otherwise described herein. Furthermore, the terms "include," "have," variations of them, and other similar terms are intended to cover a non-exclusive inclusion, such that a process, article, or apparatus that comprises a list of elements is not necessarily limited to those elements but may include other elements not expressly listed or inherent to such process, article, or apparatus.

Although certain illustrative embodiments have been disclosed, it will be apparent from the foregoing disclosure to those skilled in the art that variations and modifications of such embodiments may be made without departing from the spirit and scope of the invention. Accordingly, it is intended that the invention should be limited only to extent required by the appended claims and the rules and principals of applicable law.

What is claimed is:

1. A method comprising:
   recording, on a computer processor, a drug attribute A score to a drug based on a characteristic level of specialized clinical services associated with patient understanding of a condition that the drug is used to treat, self management of the condition that the drug is used to treat, or both the patient understanding and the self management of the condition that the drug is used to treat;
   recording, on the computer processor, a drug attribute B score to the drug based on a characteristic level of specialized requirements for intensive patient training specific to the administration of the drug or specialized requirements for administration of the drug;
   recording, on the computer processor, a drug attribute C score to the drug based on a characteristic level of specialized requirements for clinical monitoring required because of toxicity of the drug and to monitor for therapeutic effect;
   recording, on the computer processor, a drug attribute D score to the drug based on a characteristic level of an extent of specialized requirements for compliance assistance by a patient associated with the drug to facilitate therapeutic goals;
   recording, on the computer processor, a drug attribute E score to the drug based on a characteristic level of an extent of specialized requirements for handling, preparation, and storage of the drug;
   recording, on the computer processor, a drug attribute F score to the drug based on a characteristic level of a distribution channel of the drug;
   determining, on the computer processor, total value score for the drug based on the drug attribute A score, drug attribute B score, drug attribute C score, drug attribute D score, drug attribute E score, and drug attribute F score;
   determining, on the computer processor, a cost attribute for the drug based on location of a cost of the drug within a cost range of a plurality of cost ranges;
   identifying, on the computer processor, a numerical threshold value score based on the cost attribute of the drug; and
   comparing, on the computer processor, the total value score of the drug against the numerical threshold value score to identify the drug as a specialty drug.

2. The method of claim 1, wherein recording the drug attribute A score comprises:
   recording the drug attribute A score to the drug at a first characteristic level when highly specialized clinical expertise is required to support patient understanding, management, or both patient understand and management of the complex and rare condition of the patient;
   recording the drug attribute A score to the drug at a second characteristic level when specialized clinical expertise is required to support patient understanding, management, or both patient understand and management of the complex or rare condition of the patient; and
   recording the drug attribute A score to the drug at a third characteristic level when general clinical expertise is required to support patient understanding, management, or both patient understanding and management of the condition of the patient.

3. The method of claim 1, wherein recording the drug attribute B score comprises:
   recording the drug attribute B score to the drug at a first characteristic level when very intensive patient training is required specific to medication administration of the drug or when highly specialized requirements for drug administration by a healthcare professional is required;
   recording the drug attribute B score to the drug at a second characteristic level when moderately intensive patient training is required specific to medication administration of the drug or when moderately specialized requirements for drug administration by the patient is required; and
   recording the drug attribute B score to the drug at a third characteristic level when average level of patient training is required specific to medication administration of the drug or when no specialized requirements for drug administration by the patient is required.

4. The method of claim 1, wherein recording the drug attribute C score comprises:
   recording the drug attribute C score to the drug at a first characteristic level when very intensive clinical monitoring is required, including during drug administration, due to highly toxic, commonly occurring, or both highly toxic and commonly occurring adverse drug reactions associated with the drug;
   recording the drug attribute C score to the drug at a second characteristic level when moderately intensive clinical monitoring is required, including during drug administration, due to moderately toxic, less commonly occurring, or both moderately toxic and less commonly occurring adverse drug reactions associated with the drug; and
   recording the drug attribute C score to the drug at a third characteristic level when average level of clinical monitoring is required to decrease potential for drug toxicity.

5. The method of claim 1, wherein recording the drug attribute D score comprises:
   recording the drug attribute D score to the drug at a first characteristic level when compliance assistance is necessary in order to facilitate therapeutic goals;
   recording the drug attribute D score to the drug at a second characteristic level when compliance assistance is recommended in order to facilitate therapeutic goals; and
   recording the drug attribute D score to the drug at a third characteristic level when compliance assistance is optional in order to facilitate therapeutic goals.

6. The method of claim 1, wherein recording the drug attribute E score comprises:
   recording the drug attribute E score to the drug at a first characteristic level when the drug has highly specialized requirements for product handling;
   recording the drug attribute E score to the drug at a second characteristic level when the drug has moderately specialized requirements for product handling; and
   recording the drug attribute E score to the drug at a third characteristic level when the drug has no specialized requirements for product handling.

7. The method of claim 1, wherein recording the drug attribute F score comprises:

recording the drug attribute F score to the drug at a first characteristic level when the drug is only available through limited distribution channels; and recording the drug attribute F score to the drug at a second characteristic level when the drug is only available through an open distribution channel.

8. The method of claim 1, wherein recording the drug attribute A score comprises recording the drug attribute A score to the drug a value of two when highly specialized clinical expertise is required to support patient understanding, management, or both patient understanding and management of the complex and rare condition of the patient, recording the drug attribute A score to the drug a value of one when specialized clinical expertise is required to support patient understanding, management, or both patient understand and management of the complex or rare condition of the patient, and recording the drug attribute A score to the drug a value of zero when general clinical expertise is required to support patient understanding, management, or both patient understand and management of the condition of the patient;

wherein recording the drug attribute B score comprises recording the drug attribute B score to the drug a value of two when very intensive patient training is required specific to medication administration of the drug or when highly specialized requirements for drug administration by a healthcare professional is required, recording the drug attribute B score to the drug a value of one when moderately intensive patient training is required specific to medication administration of the drug or when moderately specialized requirements for drug administration by the patient is required, and recording the drug attribute B score to the drug a value of zero when average level of patient training is required specific to medication administration of the drug or when no specialized requirements for drug administration by the patient is required;

wherein recording the drug attribute C score comprises recording the drug attribute C score to the drug a value of two when very intensive clinical monitoring is required, including during drug administration, due to highly toxic, commonly occurring, or both highly toxic and commonly occurring adverse drug reactions associated with the drug, recording the drug attribute C score to the drug a value of one when moderately intensive clinical monitoring is required, including during drug administration, due to moderately toxic, less commonly occurring, or both moderately toxic and less commonly occurring adverse drug reactions associated with the drug, and recording the drug attribute C score to the drug a value of zero when average level of clinical monitoring is required to decrease potential for drug toxicity;

wherein recording the drug attribute D score comprises recording the drug attribute D score to the drug a value of two when compliance assistance is necessary in order to facilitate therapeutic goals, recording the drug attribute D score to the drug a value of one when compliance assistance is recommended in order to facilitate therapeutic goals, and recording the drug attribute D score to the drug a value of zero when compliance assistance is optional in order to facilitate therapeutic goals;

wherein recording the drug attribute E score comprises recording the drug attribute E score to the drug a value of two when the drug has highly specialized requirements for product handling, recording the drug attribute E score to the drug a value of one when the drug has moderately specialized requirements for product handling, and recording the drug attribute E score to the drug a value of zero when the drug has no specialized requirements for product handling; and wherein recording the drug attribute F score comprises recording the drug attribute F score to the drug a value of one, two, three, four, five, six, seven eight, nine, or ten when the drug is only available through limited distribution channels, and recording the drug attribute F score to the drug a value of zero when the drug is only available through an open distribution channel.

9. The method of claim 8, wherein the plurality of cost ranges include a first cost range of less than five hundred dollars per 30-day period, a second cost range of from five hundred dollars to one thousand dollars per 30-day period, and a third cost range of greater than on thousand dollars per 30-day period.

10. The method of claim 9, wherein the numerical threshold value is eight when the drug is in the first cost range, the numerical threshold is five when the drug is in the second cost range, and the numerical threshold is zero when the drug is in the third cost range.

11. The method of claim 1, wherein determining the total value for the drug comprises:
adding the drug attribute A score, the drug attribute B score, the drug attribute C score, the drug attribute D score, the drug attribute E score, and the drug attribute F score to obtain the total value for the drug.

12. The method of claim 1, wherein determining the total value for the drug comprises:
respectively weighting the drug attribute A score, the drug attribute B score, the drug attribute C score, the drug attribute D score, the drug attribute E score, and the drug attribute F score; and
adding the weighted drug attribute A score, the weighted drug attribute B score, the weighted drug attribute C score, the weighted drug attribute D score, the weighted drug attribute E score, and the weighted drug attribute F score to obtain the total value for the drug.

13. The method of claim 1, wherein determining the total value for the drug comprises:
multiplying the drug attribute A score, the drug attribute B score, the drug attribute C score, the drug attribute D score, the drug attribute E score, and the drug attribute F score to obtain the total value for the drug.

14. The method of claim 1, wherein the cost of the drug is the average wholesale price (AWP) of the drug.

15. The method of claim 1, wherein the specialty drug is dispensed through a specialty pharmacy.

16. The method of claim 1, further comprising:
receiving drug identification of the drug through a user interface, wherein recordation of the drug attribute A score is in response to receipt of the drug identification.

17. A non-transitory machine-readable medium comprising instructions, which when executed by one or more processors, cause the one or more processors to perform the following operations:
record a drug attribute A score to a drug based on a characteristic level of specialized clinical services associated with patient understanding of a condition that the drug is used to treat, self management of the condition that the drug is used to treat, or both the patient understanding and the self management of the condition that the drug is used to treat;
record a drug attribute B score to the drug based on a characteristic level of specialized requirements for intensive patient training specific to the administration of the drug or specialized requirements for administration of the drug;

record a drug attribute C score to the drug based on a characteristic level of specialized requirements for clinical monitoring required because of toxicity of the drug and to monitor for therapeutic effect;

record a drug attribute D score to the drug based on a characteristic level of an extent of specialized requirements for compliance assistance by a patient associated with the drug to facilitate therapeutic goals;

record a drug attribute E score to the drug based on a characteristic level of an extent of specialized requirements for handling, preparation, and storage of the drug;

record a drug attribute F score to the drug based on a characteristic level of a distribution channel of the drug;

determine total value for the drug based on the drug attribute A score, drug attribute B score, drug attribute C score, drug attribute D score, drug attribute E score, and drug attribute F score;

determine a cost attribute for the drug based on location of a cost of the drug within a cost range of a plurality of cost ranges;

identify a numerical threshold value based on the cost attribute of the drug; and compare the total value of the drug against the numerical threshold to identify the drug as a specialty drug.

* * * * *